United States Patent [19]

Gabellieri

[11] 4,326,035
[45] Apr. 20, 1982

[54] PROCESS FOR THE CULTURE OF AEROBIC MICROORGANISMS

[75] Inventor: Rodolfo Gabellieri, Brussels, Belgium

[73] Assignee: Interox, Brussels, Belgium

[21] Appl. No.: 868,466

[22] Filed: Jan. 9, 1978

[30] Foreign Application Priority Data

Jan. 10, 1977 [LU] Luxembourg .............................. 76547

[51] Int. Cl.$^3$ .............................................. C12N 1/32
[52] U.S. Cl. ..................................... 435/247; 435/249; 435/804; 435/818
[58] Field of Search ................ 195/28 R, 49, 27, 109, 195/114, 116; 435/249, 247, 818, 804

[56] References Cited

U.S. PATENT DOCUMENTS

| | | | |
|---|---|---|---|
| 2,120,643 | 6/1938 | Gerson | 195/109 |
| 3,041,250 | 6/1962 | Wolnak et al. | 195/109 |
| 3,126,324 | 3/1964 | Mitz et al. | 195/109 |
| 3,282,702 | 11/1966 | Schreiner | 195/109 X |
| 3,711,372 | 1/1973 | Donnelly | 195/109 X |
| 3,764,481 | 10/1973 | Muller | 195/109 |
| 3,897,303 | 7/1975 | Sherk et al. | 195/27 |

FOREIGN PATENT DOCUMENTS 1009198 5/1952 France .
861784 2/1961 United Kingdom .
914568 2/1963 United Kingdom .

OTHER PUBLICATIONS

Schlegel et al., "Production of Biomass from Hydrogen and Carbon Dioxide" Adv. in Biochem. Eng. 1971, pp. 143-168.
Schlegel, "Aeration Without Air: Oxygen Supply by Hydrogen Peroxide" Biotech. & Bioeng., 1977 vol. 19(3), pp. 413-424.

Primary Examiner—R. B. Penland
Attorney, Agent, or Firm—Spencer & Kaye

[57] ABSTRACT

Process for the culture of aerobic microorganisms in a culture medium provided with at least one source of oxygen, at least one source of carbon and at least one source of hydrogen, comprises providing oxygen originating from the decomposition of hydrogen peroxide as a source of oxygen and providing at least one highly inflammable product as a source of carbon and hydrogen.

13 Claims, 4 Drawing Figures

PROCESS FOR THE CULTURE OF AEROBIC MICROORGANISMS

BACKGROUND OF THE INVENTION

The present invention relates to a process for the culture of aerobic microorganisms.

The industrial culture of microorganisms is producing more and more positive interest. Indeed, it makes it possible to obtain the microorganisms themselves, to produce the compounds secreted by the microorganisms such as for example, enzymes, pigments or toxins, to produce metabolites such as antibiotics, vitamins or amino acids, or to transform biochemically certain defined compounds as is the case, for example, during the industrial manufacture of citric acid.

Furthermore, the use of certain microorganisms as a source of proteins for animal or human food indicates a possible solution to the world food resources crisis.

Microorganisms have in fact the advantage over plant and animal organisms usually used for food in that they have a particularly high rate of growth. This much higher productivity ought to permit a considerable increase in the quantities of food available.

Various processes have already been perfected according to which microorganisms are fed by being provided with very varied substrates to form biomasses, and protein concentrates that can be used for food are then extracted from these biomasses.

The majority of the microorganisms used for this purpose are aerobic microorganisms. The culture plants must thus be fed with air or oxygen in order to ensure the growth of the microorganisms. However, as the solubility of oxygen in water is very low, the rate of growth of microorganisms is often limited by the rate of dissolution of oxygen in the water.

In order to overcome this disadvantage, it has been proposed in British Pat. No. 861,784 filed on Jan. 10, 1958 in the name of Armour and Co. to use an aqueous solution of hydrogen peroxide as a source of oxygen. The substrates used are substrates that are currently used for the culture of microorganisms, namely, products rich in carbohydrates (molasses, peptone, glucose, lactose) or proteins. These products however have great disadvantages which make them less interesting to use as substrates from an economic point of view. Indeed, these substrates are elaborate products, some of which could be suitable such as they are, without any modifications, for animal or human food. On the other hand, certain others of these products are agricultural by-products and because of this fact complex preliminary treatments are necessary before they can be used as substrates.

In another context, for economic reasons, people have turned towards the use of substrates made up of much simpler molecules such as those derived from protroleum products. It has thus been proposed in British Pat. No. 914,568, filed on Aug. 16, 1961 in the name of British Petroleum Company Limited to grow microorganisms in the presence of oxygen and hydrocarbons such as kerosene. The extension of this process to very light substrates such as methane, methanol and mixtures of hydrogen with carbon monoxide or carbon dioxide come up against great problems due to the inflammability of the mixtures of these products with oxygen.

SUMMARY OF THE PRESENT INVENTION

There has now been found, in accordance with the present invention, a process which does not have the disadvantages of the above-mentioned processes.

The present invention provides a process for the culture of aerobic microorganisms in a culture medium provided with at least one source of oxygen, at least one source of carbon and at least one source of hydrogen, according to which oxygen originating from the decomposition of hydrogen peroxide is provided as a source of oxygen and at least one highly inflammable product is provided as a source of carbon and hydrogen.

It is to be understood that both the foregoing general description and the following detailed description are exemplary, but are not restrictive of the invention.

DETAILED DESCRIPTION OF THE INVENTION

Figure 1:
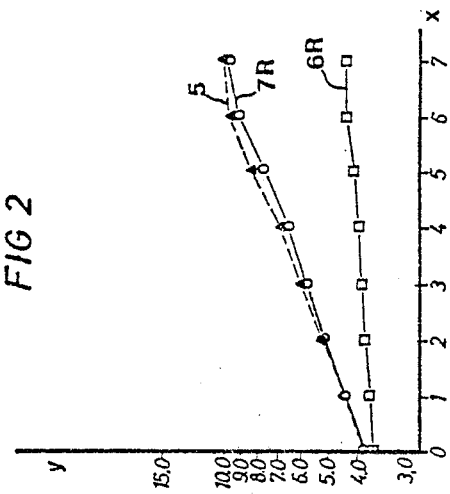
FIGS. 1 to 4 show the growth obtained, as measured by optical density, for various growing tests performed on aerobic microorganisms, with some of the tests being performed in accordance with the present invention and others being performed be way of comparison.

Generally, the highly inflammable products used according to the present invention are selected from the group consisting of light hydrocarbons, their light oxygenated derivatives, mixtures of hydrogen with carbon monoxide and mixtures of hydrogen with carbon dioxide. As used herein in the specification and claims, the term "highly inflammable products" means products whose flash point is equal to or less than 30° C. Among the light hydrocarbons, compounds containing one to eight carbon atoms are preferably used, and more particularly the saturated compounds containing 1 to 8 carbon atoms. Among the oxygenated derivatives of light hydrocarbons that are suitable for the process according to the present invention, it is preferable to use alcohols containing 1 to 4 carbon atoms and more particularly saturated aliphatic monohydric alcohols containing 1 to 4 carbon atoms. The best results are obtained with methane, methanol and mixtures of hydrogen with either carbon monoxide or carbon dioxide. The mixtures of hydrogen with carbon monoxide contain variable quantities of hydrogen, generally between 30 and 99% and preferably between 60 and 95%, by volume. The mixtures of hydrogen with carbon dioxide contain variable quantities of hydrogen, generally between 40 and 99%, and preferably between 65 and 99% by volume.

As used herein in the specification and claims, the term "culture medium" means media where microorganisms grow, media where microorganisms reproduce, or media where these two operations take place at the same time.

Generally, culture media are liquid and the microorganisms are dispersed in them. In the process according to the present invention, it is particularly preferable to effect the decomposition of hydrogen peroxide in the culture medium of microorganisms and thus in the presence of these latter.

The decomposition of hydrogen peroxide is carried out with the aid of at least one catalyst which favors the decomposition of hydrogen peroxide. These catalysts are either normal constituents of the culture medium or extraneous products which are added to the normal culture medium.

Thus, when the microorganisms contain products which favor the decomposition of hydrogen peroxide, it is not always necessary to add an extraneous catalyst. This is the case, for example, for certain bacteria and certain fungi rich in catalase. Nevertheless, the addition of small quantities of catalyst is not, however, excluded. The same is true when one of the nutrient constituents normally present in the culture medium has a catalytic effect on the decomposition of hydrogen peroxide.

When none of the constituents of the culture medium of microorganisms contain a compound which has a catalytic effect on the decomposition of hydrogen peroxide, one or more catalysts are added to the medium.

Examples of catalysts of decomposition of hydrogen peroxide which can be used in the present invention are given, for example, in the book by W. C. Shumb, C. N. Satterfield and R. L. Wentworth, Hydrogen Peroxide, A.C.S. Monograph Series No. 128, Reinhold Publishing Corp., N.Y., 1955, pages 467 to 501. Organic and biological compounds are generally well suited. Among these, catalase and peroxidase, which are well known for their high activity, are preferably used.

The quantity of hydrogen peroxide to be used should be determined in terms of the maximum rate of decomposition of hydrogen peroxide that can be obtained in the culture conditions such that there is no excess hydrogen peroxide present in the medium.

This maximum admissible rate depends notably on the nature of the catalyst.

If the catalyst used is sufficiently effective and the quantity of oxygen formed can be higher than that necessary for the growth of microorganisms, the quantity of hydrogen peroxide introduced must be determined in terms of the oxygen needs of the microorganisms in such a way as to satisfy them without exceeding them unduly. These oxygen needs of microorganisms depend notably on the type of microorganisms, their concentration in the culture medium and on the substrate used as a nutrient element.

The quantity of hydrogen peroxide introduced into the culture medium per unit of time usually varies between 10 and 10,000 micromoles per mg of dry microorganisms formed per unit of time. The nature of the strain of microorganisms used can entail the use of lesser or greater quantities of hydrogen peroxide. The use of substrates that are rich in carbon and hydrogen and lacking in oxygen implies a greater oxygen consumption.

In the practice of the present invention, hydrogen peroxide is generally used in the form of solutions in a solvent compatible with hydrogen peroxide and the culture medium. Water is generally used as a solvent. Although it is possible to use solutions of very varied concentrations, it is preferable to use dilute solutions containing, in general, less than 10% and preferably 0.005 to 8% by weight hydrogen peroxide. Very low concentrations obviously require large equipment. Higher concentrations are not advisable because it is necessary to avoid risk of local accumulation of hydrogen peroxide, which could lead to the death of the microorganisms, if there is insufficient agitation.

The hydrogen peroxide is preferably introduced directly into the culture medium. It is also possible to use other processes enabling the nascent oxygen originating from the decomposition of hydrogen peroxide to come into contact with the culture medium.

It is possible, for example, to introduce the hydrogen peroxide in solution into the nutrient medium which is usually an aqueous solution, and to send all of it directly into the culture medium. Other processes can also be used.

The process according to the present invention can be applied to the culture of all strict or facultative aerobic microorganisms capable of assimilating the substrates that can be used according to the present invention. Such organisms are chemotrophic as they draw the necessary energy for biological synthesis from fermentation reactions of organic compounds or from oxidation of organic or inorganic compounds. The process which is the object of the present invention is preferably applied to chemoorganotrophic microorganisms. Among these there are a large number of bacteria, such as, for example, the majority of pseudomonales and actinomycetales, numerous fungi, such as, for example, the majority of the phycomycetes and ascomycetes including especially the saccharomycetes or yeasts, protozoa as well as different types of animal cells.

The process according to the present invention can be applied particularly well to the culture of unicellular microorganisms.

The following types of bacteria can be pointed out as bacteria that have an industrial interest to which the process which is the object of the present invention can be applied: acetobacter, acetomonas, arthrobacter, brevibacterium, corynebacterium, hydrogenomonas, micrococcus, micobacterium, nocardia, pseudomonas, streptomyces, vibrio, and the like. The following types, more particularly, can be mentioned as fungi or yeasts: aspergillus, candida, cryptococcoidees, penicillium, saccharomyces, torulopsis, and the like.

The type of microorganisms to be cultivated is obviously directly linked with the nature of the substrate which one wants to use. Thus, if one wants to use methane as a substrate for the production of proteins, it will be advantageous to use microorganisms of the bacteria type such as pseudomonas. If the substrate is methanol, the best results are obtained with yeasts of the candida type or bacteria of the pseudomonas type. If the substrate is a mixture of hydrogen and carbon monoxide or carbon dioxide, the best results are obtained with bacteria of the hydrogenomonas type.

The nutrient media in which the culture of microorganisms can take place are fairly complex and diversified. Apart from the substrate and oxygen, they contain notably a certain number of nutritive mineral products containing elements such as nitrogen, potassium, calcium, magnesium, sulfur and phosphorus, for example, as well as small quantities of other oligo-elements that are essential for development such as, for example, zinc, iron, copper and cobalt.

The nature of the microorganism also determines the temperature and the pH at which culture is effected. In general, the optimum culture temperature is in the order of 37° C. for a large number of bacteria, and 28° C. for a large number of fungi. Certain microorganisms, however, require lower or higher culture temperatures. The pH values usually vary between 4 and 8, the bacteria having an optimal growth around pH 7 whereas fungi require a pH of 4 to 5. Given that during the culture of microorganisms the formation of various products likely to modify the pH of the culture medium is observed, it is often necessary to add to the culture medium buffers or other agents capable of maintaining the pH at its optimum value.

The process that is the object of the present invention can be carried out continuously or discontinuously. Various types of apparatus can be used for this purpose. They are generally fitted with means of agitation and means of controlling the temperature in such a way as to avoid any increase in the temperature which could be fatal for the cultures.

The process of the present invention has enabled microorganisms to be cultivated with an excellent rate of growth. It also enables any risk of ignition of the substrates used to be avoided, and enables the use of substrates which are made up of relatively simple molecules.

The following examples are given by way of illustration to further explain the principles of the invention. These illustrative examples are not to be understood as limiting the scope and underlying principles of the invention in any way. All percentages referred to herein are by weight unless otherwise indicated.

The following examples show the remarkable results obtained according to one method of carrying out the present invention.

The following examples were carried out by Dr. Bernhard Schink under the supervision of Professor Dr. H. G. Schlegel, Director of the Institut für Microbiologie of the University of Göttingen, Grisebachstr. 8, 3400 Göttingen, West Germany at applicant's request.

Examples 1, 2 and 3 were carried out using methanol as a substrate and Example 4 was carried out using a mixture of hydrogen and carbon dioxide as a substrate.

EXAMPLE 1

A quantity of 30 ml of aqueous solution containing mineral compounds, 0.2% extract of DIFCO yeast, 0.5% methanol, 0.1 mg biotin per liter, 1.0 mg thiamine per liter and 0.09 ml catalase, i.e. 90,000 international units per ml is introduced into a wide-necked Erlenmeyer flask.

The mineral elements content per liter of aqueous solution is as follows:

| | | | |
|---|---|---|---|
| —$NH_4Cl$ | 1 g | —$MgSO_4 . 7H_2O$ | 0.2 g |
| —$Na_2HPO_4 . 12H_2O$ | 9.0 g | —$FeNH_4$-citrate | 5 mg |
| —$KH_2PO_4$ | 1.5 g | —$CaCl_2 . 2H_2O$ | 10 mg |

Yeasts of the candida biodinii type are injected into the medium in quantities such that the initial optical density of the suspension measured at 436 nm, is 0.7.

A current of nitrogen free from oxygen sweeps the empty space of the culture container.

The temperature of the culture is maintained at 30° C. by means of a thermostat and the culture medium is agitated by an agitator turning at 100 r.p.m.

An aqueous solution of 0.3% hydrogen peroxide is introduced into the medium at a rate of 2.5 ml/hr. (test 1) and 5 ml/hr (test 2), respectively. An oxygen electrode immersed into the medium enables the free oxygen content to be controlled.

Every hour a sample from the culture medium is taken and the development of the weight of microorganisms is calculated from optical density measurements of the samples taken.

In the two tests, the time needed for the weight of microorganisms to double is 3.5 hr. Exponential growth was continued for 7 hours. The results obtained are shown in curves 1 and 2 of FIG. 1 where the abscissa x represents the time expressed in hours and the y coordinate represents the optical density.

By way of comparison, a test (test 3R) was carried out without hydrogen peroxide and catalase being introduced, all the other conditions being identical to those in tests 1 and 2. No growth of the microorganisms was observed. The results obtained are also shown in FIG. 1 by curve 3R.

By way of comparison, another test (test 4R) was carried out without introducing hydrogen peroxide and catalase. The free space of the culture container is swept by a current of air at a rate of 0.5 l/min. The other conditions are identical to those in tests 1,2 and 3R. The results obtained are shown in FIG. 1 by curve 4R.

Examination of the tests shown in FIG. 1 shows that the replacement of oxygen by hydrogen peroxide does not alter the growth of candida biodinii.

EXAMPLE 2

A quantity of 200 ml of aqueous solution containing the same mineral compounds, and these in the same proportion as in Example 1, as well as 0.5% methanol, 0.1 mg. biotin per liter, 1.0 mg thiamine per liter, 0.63 ml catalase and 0.2% DIFCO yeast extract is introduced into a wide-necked Erlenmeyer flask.

Yeasts of the candida biodinii type are injected into the medium in proportions such that the initial optical density of the suspension, measured at 436 nm, is 3.9.

A current of nitrogen free from oxygen sweeps the free space of the culture vessel.

The culture temperature is maintained at 30° C. by means of a thermostat and the culture medium is agitated by an agitator turning at 800 r.p.m.

An aqueous solution of 4% hydrogen peroxide is introduced into the medium in a ratio of 3.8 and finally 5.4 ml/hr (test 5). An oxygen electrode immersed into the medium enables the free oxygen content to be maintained at 2 ml oxygen per liter.

Every hour the development of the weight of microorganisms is controlled as in Example 1.

The time needed for the weight of microorganisms to double is 4.8 hours. The results obtained are shown in curve 5 of FIG. 2 where x and y have the same designation as in FIG. 1.

Two comparative tests were carried out with the same medium as in test 5 in the absence of hydrogen peroxide and catalase under a current of nitrogen (test 6R) and a current of air (test 7R), respectively. The results obtained are shown in curves 6R and 7R, respectively, in FIG. 2.

Figure 2:
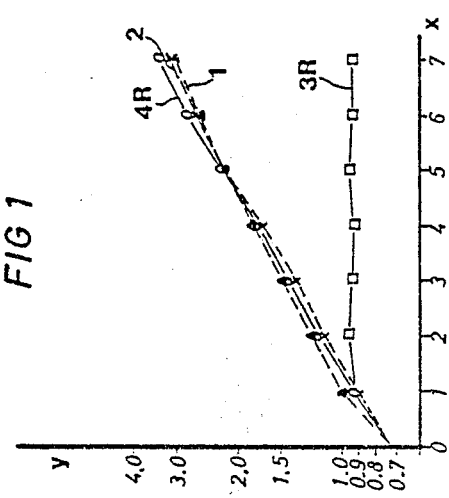

Examination of the results shown in FIG. 2 shows that hydrogen peroxide is very slightly more effective in relation to oxygen as regards the growth of microorganisms.

EXAMPLE 3

A quantity of 200 ml of an aqueous solution containing the same mineral compounds, and these in the same proportion as in Example 1, as well as 1.0% methanol, 0.1 mg biotin per liter and 0.63 ml catalase is introduced into a wide-necked Erlenmeyer flask.

Pseudomonas of the Finn strain are injected into the medium.

The working conditions are identical to those in test 5 of Example 2. The aqueous solution of 4% hydrogen peroxide is introduced into the medium at a ratio of 3.5 ml/hr (test 8). An oxygen electrode immersed into the medium enables the free oxygen content to be maintained at 2 mg oxygen per liter.

The time needed for the weight of microorganisms to double is about 5 hours. The results obtained are shown in FIG. 3 where x and y have the same designation as in FIG. 1.

Two comparative tests were carried out with the same medium as in test 8, in the absence of hydrogen peroxide and catalase under a nitrogen current (test 9R) and an air current (test 10R), respectively. The results obtained are shown in curves 9R and 10R, respectively, in FIG. 3.

Figure 3:
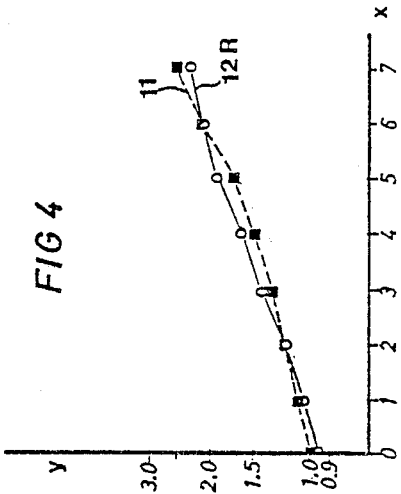

Examination of the results shown in FIG. 3 shows that hydrogen peroxide is very slightly more effective in relation to oxygen as regards the growth of microorganisms.

EXAMPLE 4

A quantity of 200 ml of an aqueous solution containing the same mineral compounds, and these in the same proportions as in Example 1, and 0.45 ml catalase is introduced into a wide-necked Erlenmeyer flask.

A strain of bacteria of the *alcaligenes eutrophus* (≡hydrogenomonas) H16 mutant PHB$^{-4}$ type is injected into the medium.

A gaseous current containing 90% hydrogen and 10% carbon dioxide sweeps the empty space of the culture vessel.

The culture temperature is maintained at 30° C. by means of a thermostat and the culture medium is agitated by an agitator turning at 800 r.p.m.

A solution of 4.8% hydrogen peroxide is introduced into the medium in a ratio of 2 ml/hr (test 11). An oxygen electrode immersed in the medium enables free oxygen content to be regulated.

Every hour a sample of the culture medium is taken and the development of the weight of microorganisms is calculated from optical density measurements of the samples taken.

The time needed for the weight of microorganisms to double is about 5 hours. The results obtained are shown by curve 11 in FIG. 4, where x and y have the same designation as in FIG. 1.

A comparative test (test 12R) was carried out with the same medium as in test 11 in the absence of hydrogen peroxide and catalase and under a gaseous current containing 70% hydrogen, 10% carbon dioxide and 20% oxygen. The results obtained are shown in curve 12R in FIG. 4.

Figure 4:
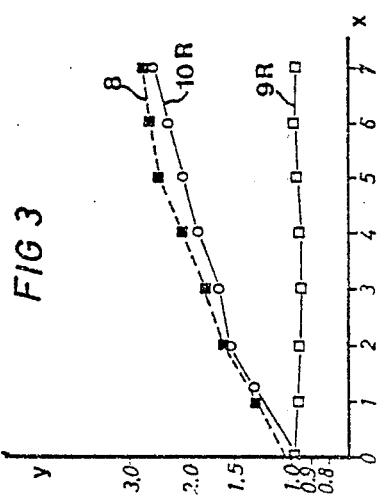

Examination of the results shown in FIG. 4 shows that the replacement of oxygen by hydrogen peroxide enables approximately the same results to be obtained for the culture of *alcaligenes eutrophus* H16 PHB$^{-4}$.

It will be understood that the above description of the present invention is susceptible to various modifications, changes and adaptations, and the same are intended to be comprehended within the meaning and range of equivalents of the appended claims.

What is claimed is:

1. Process for the culture of aerobic microorganisms in a culture medium provided with at least one source of oxygen, and with a highly flammable substrate comprised of at least one source of carbon and at least one source of hydrogen, consisting essentially of: providing oxygen originating from the decomposition of hydrogen peroxide as a sole added source of molecular oxygen and providing said highly inflammable substrate as a substrate having a flash point equal to or less than 30° C., said hydrogen peroxide being provided in the form of an aqueous solution in an amount such that oxygen is formed in a quantity sufficient to satisfy the growth needs of the microorganisms, whereby the risk of ignition of the substrate used is avoided.

2. Process according to claim 1, wherein the source of carbon and hydrogen is selected from the group consisting of light saturated hydrocarbons having one to eight carbon atoms, oxygenated derivatives of said light hydrocarbons, a mixture of hydrogen with carbon monoxide, and a mixture of hydrogen with carbon dioxide.

3. Process according to claim 2, wherein the source of hydrogen and carbon is said light hydrocarbon.

4. Process according to claim 2, wherein the source of carbon and hydrogen is methane.

5. Process according to claim 2, wherein the source of carbon and hydrogen is an oxygenated derivative of said light hydrocarbon.

6. Process according to claim 5, wherein the source of carbon and hydrogen is a saturated aliphatic monohydric alcohol containing 1 to 4 carbon atoms.

7. Process according to claim 6, wherein the source of carbon and hydrogen is methanol.

8. Process according to claim 2, wherein the source of carbon and hydrogen is a mixture of hydrogen and carbon dioxide containing 40 to 99% by volume hydrogen.

9. Process according to claim 1, wherein the decomposition of hydrogen peroxide is carried out in the culture medium.

10. Process according to claim 9, wherein the hydrogen peroxide is added directly to the culture medium.

11. Process according to claim 10, wherein the aqueous solution contains less than 10% by weight hydrogen peroxide.

12. The process according to claim 9 wherein the quantity of hydrogen peroxide introduced into said culture medium is 10 to 10,000 micromoles per milligram of dry microorganisms.

13. Process according to claim 1, wherein the decomposition of hydrogen peroxide is carried out with the aid of a catalyst.

* * * * *